(12) United States Patent
Zetterström

(10) Patent No.: US 10,546,100 B2
(45) Date of Patent: Jan. 28, 2020

(54) TABLET DISPENSER

(71) Applicant: Medicpen AB, Lomma (SE)

(72) Inventor: Åke Zetterström, Lomma (SE)

(73) Assignee: Medicpen AB, Lomma (SE)

( * ) Notice: Subject to any disclaimer, the term of this patent is extended or adjusted under 35 U.S.C. 154(b) by 0 days.

(21) Appl. No.: 15/617,910

(22) Filed: Jun. 8, 2017

(65) Prior Publication Data

US 2018/0353385 A1 Dec. 13, 2018

(51) Int. Cl.
| | |
|---|---|
| A61J 7/00 | (2006.01) |
| G07F 11/62 | (2006.01) |
| B65D 83/04 | (2006.01) |
| G06F 19/00 | (2018.01) |
| G07F 17/00 | (2006.01) |
| G07F 11/32 | (2006.01) |
| A61J 7/04 | (2006.01) |
| G07F 11/44 | (2006.01) |

(52) U.S. Cl.
CPC ........ *G06F 19/3462* (2013.01); *A61J 7/0454* (2015.05); *G07F 11/32* (2013.01); *G07F 11/44* (2013.01); *G07F 11/62* (2013.01); *G07F 17/0092* (2013.01); *A61J 2205/10* (2013.01)

(58) Field of Classification Search
CPC ..... A61J 7/0076; G07F 11/24; G06F 19/3462
See application file for complete search history.

(56) References Cited

U.S. PATENT DOCUMENTS

| | | | |
|---|---|---|---|
| 3,998,356 A * | 12/1976 | Christensen | ......... A61J 7/0481 221/2 |
| 4,047,635 A | 9/1977 | Bennett, Jr. | |
| 4,087,020 A | 5/1978 | Krakauer | |
| 4,207,992 A | 6/1980 | Brown | |

(Continued)

FOREIGN PATENT DOCUMENTS

| | | |
|---|---|---|
| DE | 212012000067 U1 | 12/2013 |
| EP | 1174363 A1 | 1/2002 |

(Continued)

OTHER PUBLICATIONS

Medicpen video file, "Medication errors have cost enough," available on the internet at https://www.dropbox.com/sh/auw5k4slq5q9ucu/AACVOWdnBvYXtsBqXLTQGll6a?dl=0, Danish version uploaded to youtube by Medicpen employee on Jun. 9, 2016, English version uploaded to youtube by Medicpen employee on Jul. 13, 2016.

(Continued)

*Primary Examiner* — Gene O Crawford
*Assistant Examiner* — Kelvin L Randall, Jr.
(74) *Attorney, Agent, or Firm* — Capitol City TechLaw (57) ABSTRACT

A tablet dispenser may include a body having a base for resting on an underlying foundation in use. The body may include a tablet drop channel that extends in a direction at an angle ($\beta$) relative a base plane formed by the base, and a support structure for accommodating at least two tablet cartridge units may be arranged one above the other in relation to the base. Each tablet cartridge unit may have an opening allowing a tablet from the associated tablet cartridge unit to be released into the tablet drop channel via gravitational force, whereby each tablet cartridge unit is inclined at an angle ($\alpha$) relative the base plane.

12 Claims, 7 Drawing Sheets

(56) References Cited

U.S. PATENT DOCUMENTS

| | | | | |
|---|---|---|---|---|
| 4,809,877 | A * | 3/1989 | Albright | A61J 7/0481 221/121 |
| 4,811,764 | A * | 3/1989 | McLaughlin | A61J 7/0084 141/104 |
| 4,911,327 | A * | 3/1990 | Shepherd | A61J 7/0481 221/15 |
| 4,953,745 | A | 9/1990 | Rowlett, Jr. | |
| 5,176,285 | A | 1/1993 | Shaw | |
| 5,522,525 | A * | 6/1996 | McLaughlin | A61J 7/0481 221/4 |
| 5,667,096 | A * | 9/1997 | Wu | G07F 11/32 221/130 |
| 5,755,357 | A | 5/1998 | Orkin et al. | |
| 6,006,946 | A | 12/1999 | Williams et al. | |
| 6,427,865 | B1 * | 8/2002 | Stillwell | G07F 11/54 221/113 |
| 6,684,126 | B2 | 1/2004 | Omura et al. | |
| 6,805,259 | B2 * | 10/2004 | Stevens | B65B 5/103 198/757 |
| 9,245,093 | B2 | 1/2016 | Shaw | |
| 9,597,261 | B2 * | 3/2017 | Baarman | A61J 7/0084 |
| 2003/0231119 | A1 * | 12/2003 | Chiavetta | A61J 7/0084 340/870.07 |
| 2004/0182873 | A1 | 9/2004 | Baum | |
| 2007/0078410 | A1 * | 4/2007 | Chiavetta | A61J 7/0084 604/214 |
| 2008/0164274 | A1 * | 7/2008 | Stettes | A47J 31/401 221/5 |
| 2010/0030374 | A1 | 2/2010 | Saltsov | |
| 2013/0073078 | A1 * | 3/2013 | Handfield | A61J 7/0084 700/241 |
| 2013/0253700 | A1 | 9/2013 | Carson et al. | |
| 2014/0277702 | A1 | 9/2014 | Shaw | |
| 2015/0266654 | A1 * | 9/2015 | Baarman | B65D 83/0409 221/190 |
| 2016/0008226 | A1 * | 1/2016 | Hines | A61J 7/0084 221/12 |
| 2018/0104153 | A1 * | 4/2018 | Wang | A61J 7/0069 |

FOREIGN PATENT DOCUMENTS

| | | |
|---|---|---|
| EP | 2752182 A1 | 7/2014 |
| KR | 101355138 B1 | 1/2014 |
| WO | 0063857 A1 | 10/2000 |
| WO | 2015196293 A1 | 12/2015 |

OTHER PUBLICATIONS

Medicpen video file—Updated, "Medication errors have cost enough", Danish version available on the Internet at https://www.youtube.com/watch?v=ic-BCEFXg24, English version available on the Internet at https://www.youtube.com/watch?v=o-QdAXpeuCE, Apr. 24, 2017.

* cited by examiner

TABLET DISPENSER

BACKGROUND

1. Field

The present invention relates in general to medical dispensers, and in particular to multiple cartridge medical tablet dispensers for private or hospital use.

2. Discussion of Related Art

Medical tablet dispensers are used in both clinics and home care in an attempt to improve compliance with and monitoring of medication. The compliance is improved by only allowing the patient to dispense a correct amount and type of tablets based on a dosing regimen being accessible to the medical tablet dispenser. Since many patients require several types of medicines there is an urge to provide medical tablet dispensers being capable of dispensing different types of medicines from a single tablet dispenser.

Although many solutions are known, typically such multiple tablet type dispensers are mechanically rather complex in order to allow different types of tablets to be dispensed from the single unit.

An improved tablet dispenser unit being less complex than conventional units, and providing for improved robustness would be advantageous.

SUMMARY

An object of the invention is to at least alleviate the above stated problem.

According to an aspect a tablet dispenser is provided. The tablet dispenser unit comprises a body having a base for resting on the underlying foundation in use. The body comprises a tablet drop channel extending in a direction at an angle relative a base plane formed by the base. Moreover, the body comprises a support structure for accommodating at least two tablet cartridge units arranged one above the other in relation to the base, each tablet cartridge unit having an opening allowing a tablet from the associated tablet cartridge unit to be released into the tablet drop channel by means of gravitational force, whereby each tablet cartridge unit is inclined at an angle relative the base plane.

According to another aspect a tablet cartridge unit is provided. The tablet cartridge unit comprises a compartment member having a cylindrical cover sheet on which an inner wall is arranged, wherein a number of flexible flanges are arranged on the cylindrical cover sheet between the inner wall and an outer boundary of the cover sheet. Moreover, the tablet cartridge unit comprises an associated socket for receiving the compartment member in use, wherein the socket comprises a cylindrical socket base plate and an outer wall extending at least partly along an outer boundary of the socket base plate, the outer wall having an inner diameter being larger than the outer diameter of the cover sheet, thereby allowing the socket to embrace the compartment member in use, whereby two adjacent flanges, the inner wall, the cover sheet, the outer wall, and socket base plate forms a tablet compartment for holding at least one tablet. The socket base plate comprises means for detachably attaching the cylindrical inner wall of the associated compartment member to the socket, such that the compartment member when attached is allowed to rotate in relation to the socket such as to allow for rotary alignment of each tablet compartment and the opening.

BRIEF DESCRIPTION OF THE DRAWINGS

The above, as well as additional objects, features and advantages of the present invention, will be better understood through the following illustrative and non-limiting detailed description of preferred embodiments of the present invention, with reference to the appended drawings.

DESCRIPTION OF NON-LIMITING EMBODIMENTS

Figure 1A:
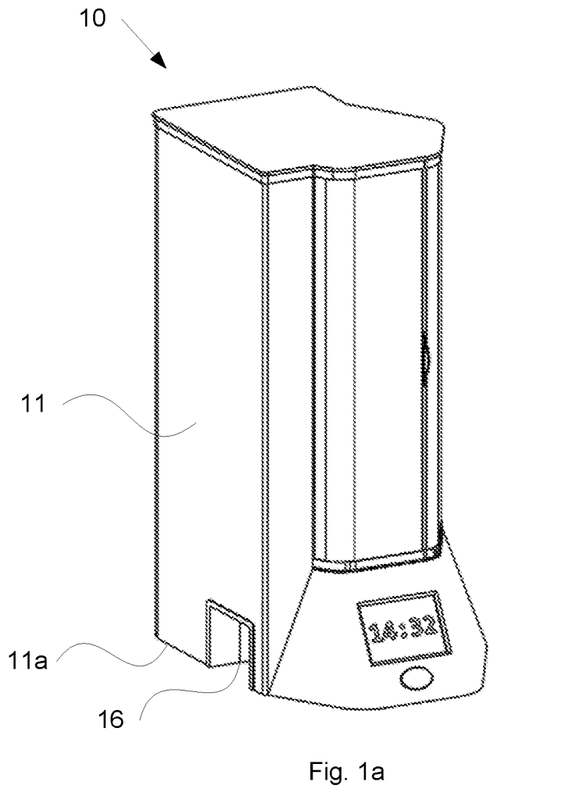
FIGS. 1a and 1b respectively show isometric views taken from different viewing angles of a tablet dispenser as provided for herein.
Figure 1B:
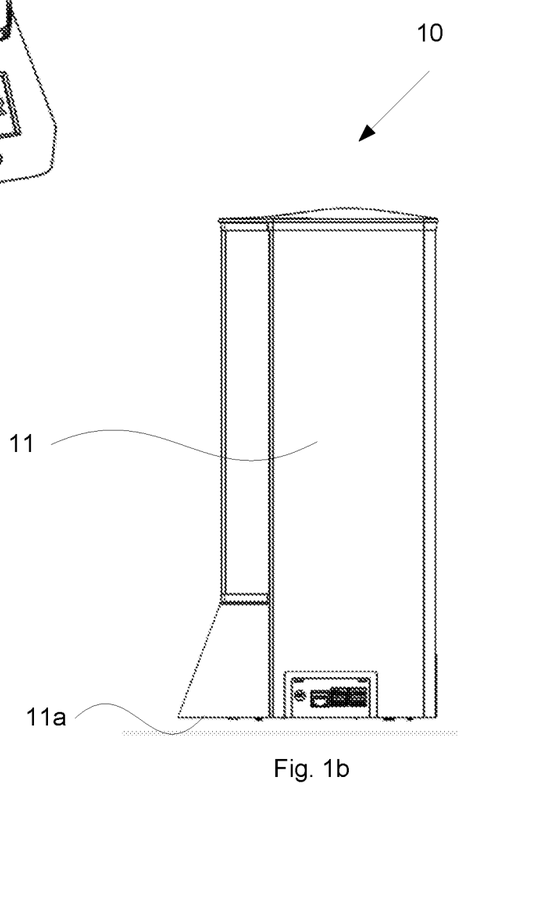

With reference to FIGS. 1a and 1b a tablet dispenser 10 is provided. The tablet dispenser comprises a body 11 having a base 11a for resting on the underlying foundation in use. The body 11 comprises a tablet drop channel 12 extending in a direction at an angle β relative a base plane formed by the base 11a. In normal use the base plane is aligned with a horizontal top surface of e.g. a table or desk, whereby the tablet drop channel extends along a direction having a component in along the vertical axis of said plane. The body 11 further comprises a support structure 13 for accommodating at least two tablet cartridge units 15 arranged one above the other in relation to the base 11a. Each tablet cartridge unit is provided with an opening 15B allowing a tablet stored in a tablet compartment of said tablet cartridge unit 15 to be released into the tablet drop channel 12 by means of gravitational force. To this end, each tablet cartridge unit 15 is inclined at an angle α relative the base plane. Hence, both the drop channel and the tablet cartridge unit are respectively arranged at an angle relative the base plane.

Figure 2A:
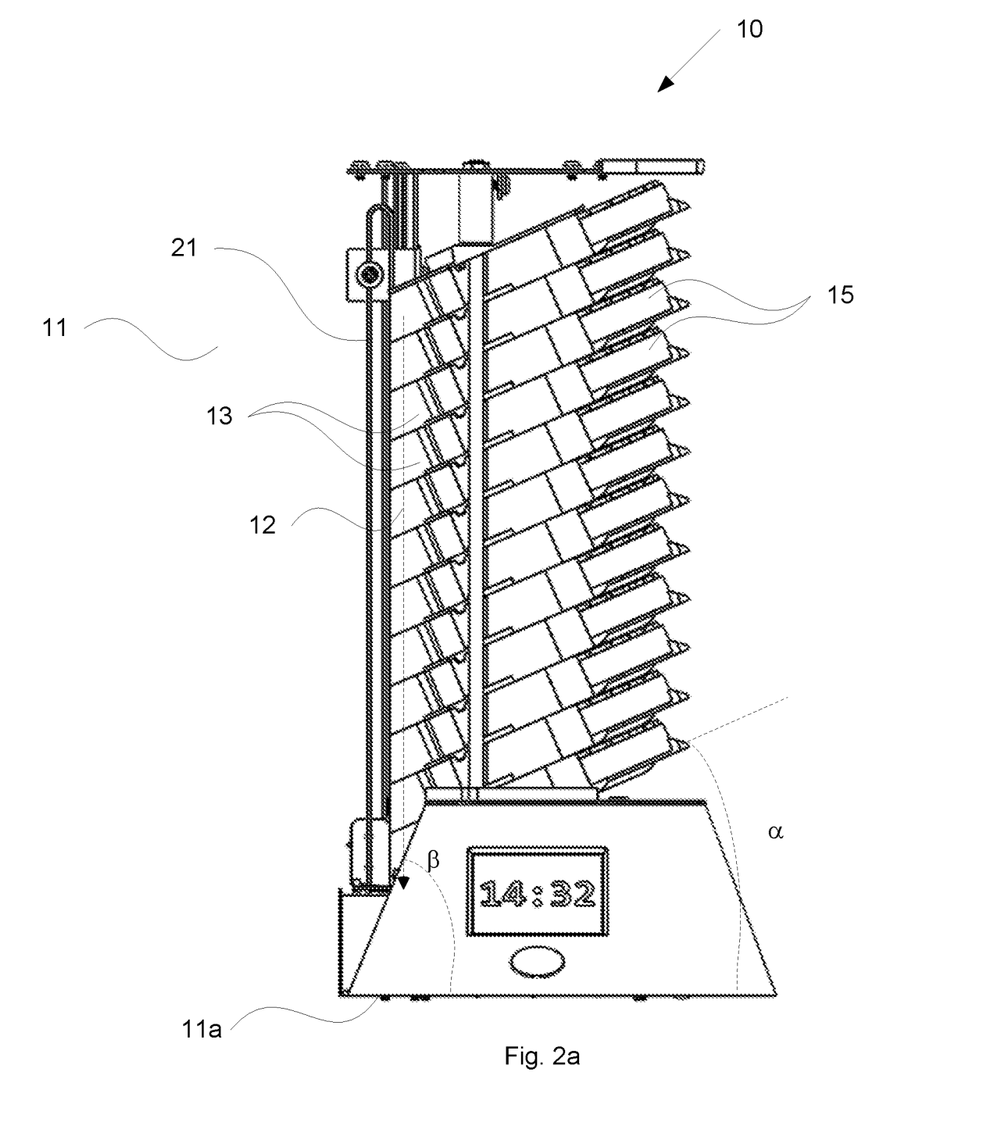
FIGS. 2a to 2d respectively show isometric views taken from different viewing angles of a tablet dispenser provided herein where the outer cover has been removed.
Figure 2B:
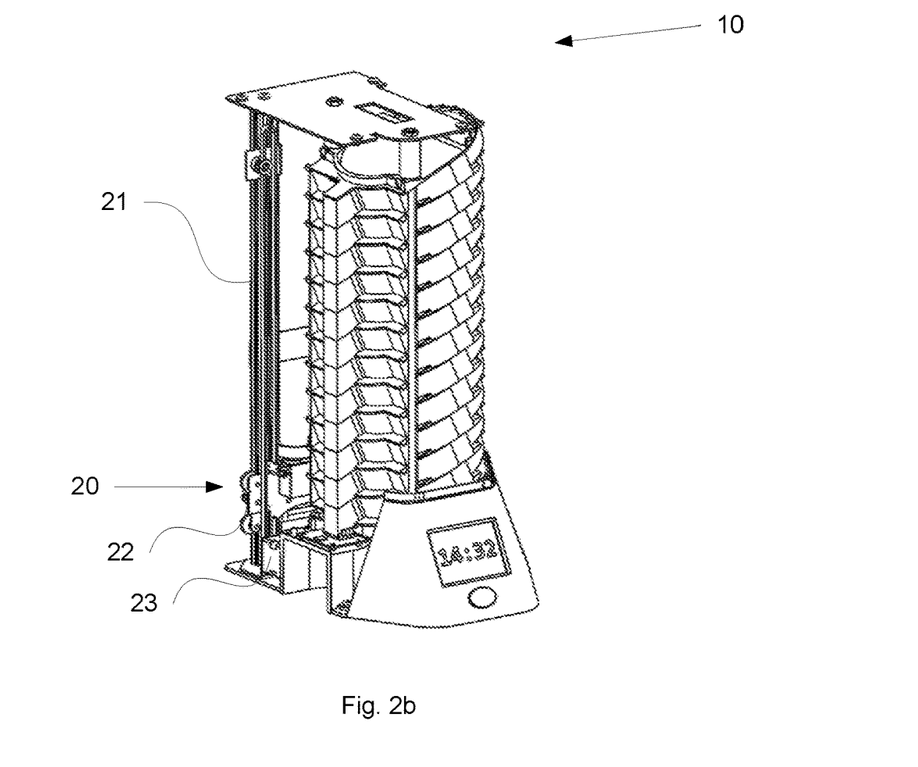

Preferably the inclination angle α, as perhaps best seen in relation to the cross sectional view of FIG. 2a, of the respective tablet cartridge unit in relation to the base plane is smaller than the angle β between the extension of the drop channel and that of the base plane. In some conditions the extension of the tablet drop channel is close to orthogonally arranged in relation to the base plane. As seen in FIGS. 2a to 2d a cover of the body has been removed to better show the inner structure of the tablet dispenser.

Figure 3A:
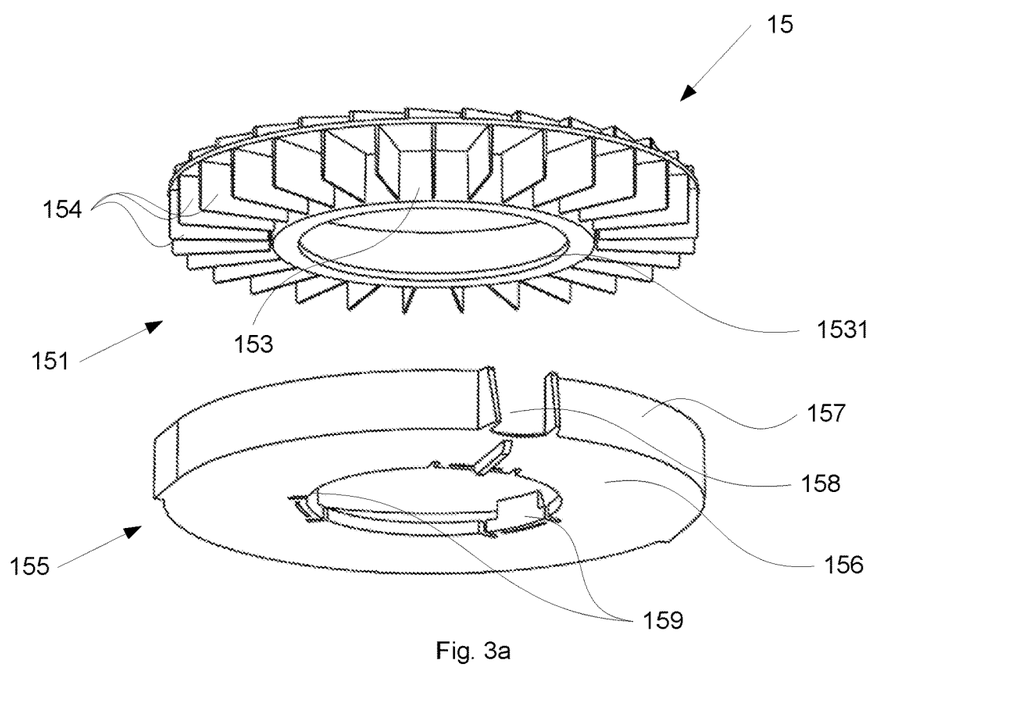
FIGS. 3a and 3b respectively show isometric views taken from different viewing angles of a tablet cartridge unit as provided for herein.
Figure 3B:
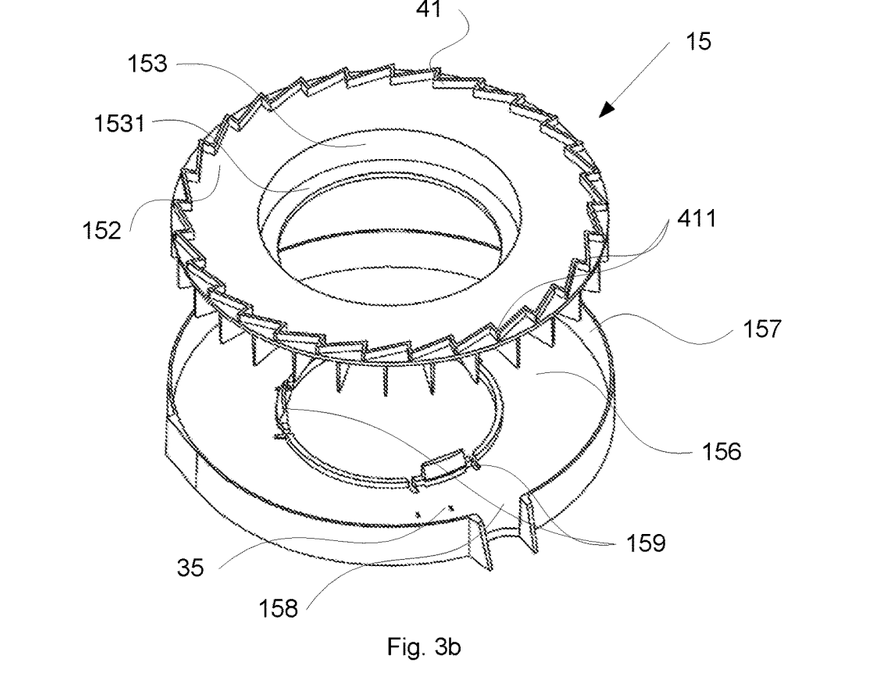

As seen in the bottom portion of FIG. 1b, the tablet dispenser may comprise a power connector, including optional communication interfaces, such as Ethernet, USB connecting the tablet dispenser to an external device, for external monitoring, remote updating of dosing regimens, etc. Also a display for providing useful information to the user and a dispensing button may be provided on the tablet dispenser unit as seen in FIG. 1a. With reference to FIGS. 3a to 4b, each tablet cartridge unit 15 comprises a compartment member 151 having a cylindrical cover sheet 152 on which an inner wall 153 is arranged. A number of flexible flanges 154 are arranged on the cylindrical cover sheet 152 between the inner wall 153 and an outer boundary of the cover sheet 152. Hence the flanges 154 extend radially from the inner wall 153 towards the outer boundary of the cover sheet 152, as best seen in the top part of FIG. 3a. Moreover, each tablet cartridge unit 15 further comprises an associated socket 155 for detachably receiving the compartment member 151 before use. The socket 155 comprises a cylindrical socket base plate 156 and an outer wall 157 extending at least partly along an outer boundary of the socket base plate 156. The opening 158 may be provided straight through the outer wall 157 at one part thereof, as best shown in FIGS. 3a and 3b. The outer wall 157 having an inner diameter being larger than the outer diameter of the cover sheet 152, thereby allowing the socket 155 to embrace the compartment member 151 upon assembly. When assembled a tablet compartment for holding at least one tablet is formed between two adjacent flanges 154, the inner wall 153, the cover sheet 152, the outer wall 157, and the socket base plate 156. Because the compartment member 151 comprises a number of flanges 154 several tablet compartments are formed upon assembly in the space between the compartment member 151 and the respective socket 155.

Each tablet cartridge unit may be prefilled with tablets e.g. prior to reaching the end-consumer. Each tablet cartridge unit may be prefilled by placing a tablet in the associated spaces between two flanges 154 of the compartment member 151 and upon completion gently pressing the associated socket 155 over the compartment member whereby the tablet cartridge is assembled. A means of identification, e.g. a QR code, ID tag, label, etc. indicating the type of tablets in the tablet cartridge unit may be provided on the exterior side of the outer wall 157. Such a means for identification may be read before using the tablet dispenser, such that the tablet dispenser knows the type of medication stored in each tablet cartridge unit. The means for identification, e.g. the QR code, may contain information such as patient ID, drug ID, amount of tablets, start/end date for medication, cartridge serial number.

As seen in FIGS. 3a and 3b the inner wall 153 may have a cylindrical shape. The socket base plate 156 comprises means 159 for detachably attaching the inner wall 153 of the associated compartment member 151 to the socket 155. In this way the compartment member 151 when assembled is allowed to rotate in relation to the socket 155 such as to allow for rotary alignment of each tablet compartment and the opening 158 in use.

As seen in FIGS. 3a and 3b the means 159 for detachably attaching the inner wall 153 to the socket may e.g. comprise snap locks or clamps 159 provided on the socket 155 for engaging with a flange 1531 extending radially from the inner wall 153 of the compartment member 151.

Figure 4A:
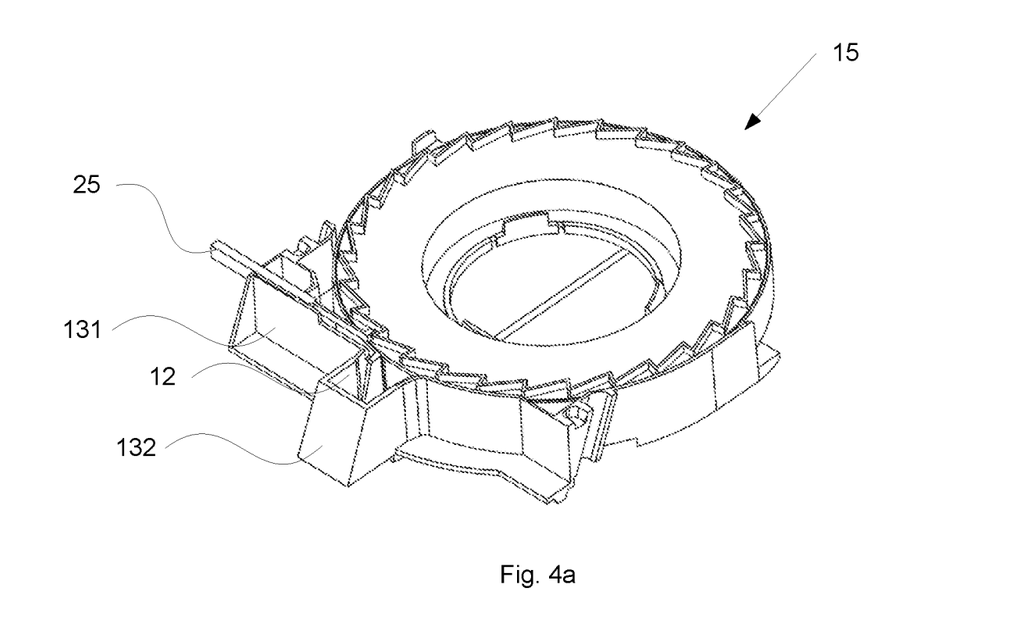
FIGS. 4a and 4b respectively show isometric views taken from different viewing angles of the tablet cartridge unit of FIGS. 3a and 3b when assembled and mounted into a cartridge receiving member of the associated supporting structure.
Figure 4B:
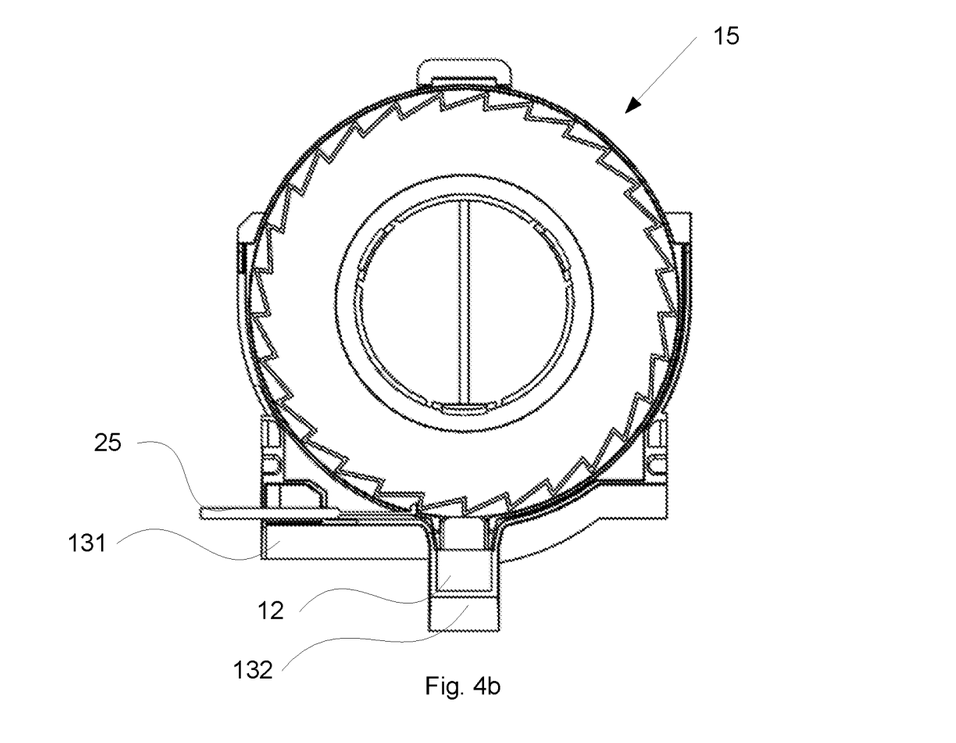

The cover sheet 152 comprises a cylindrical ridge pattern 41 provided at a side opposite that of the inner wall 153 and flexible flanges 154. The cylindrical ridge pattern has one engagement surface 411 for each tablet compartment. Hence, the number of engagement surfaces 411 is equal to the number of flanges 154 of the compartment member 151. Each engagement surface 411 in use is arranged to receive a force, e.g. from a spring loaded telescoping pushing member 25 as shown in FIGS. 4a and 4b, such to rotate the compartment member 151 in relation to its associated socket 155, thereby aligning the opening 158 with the tablet compartment being next in order of the tablet cartridge unit.

The socket base plate 156 may be provided with a protrusion 35 protruding in a direction having a component in the same direction as the outer wall 157, as perhaps best shown in the bottom part of FIG. 3b. The protrusion, which may be provided as a rounded protrusion, is in use arranged to engage with one of the flexible flanges 154 when said flange 154 is moved thereover upon its rotary movement in relation to the socket 155 such as to bend the flexible flange such as to increase the size tablet compartment, to avoid a tablet from getting stuck in the tablet compartment when the tablet compartment is aligned with the opening 158.

Figure 5A:
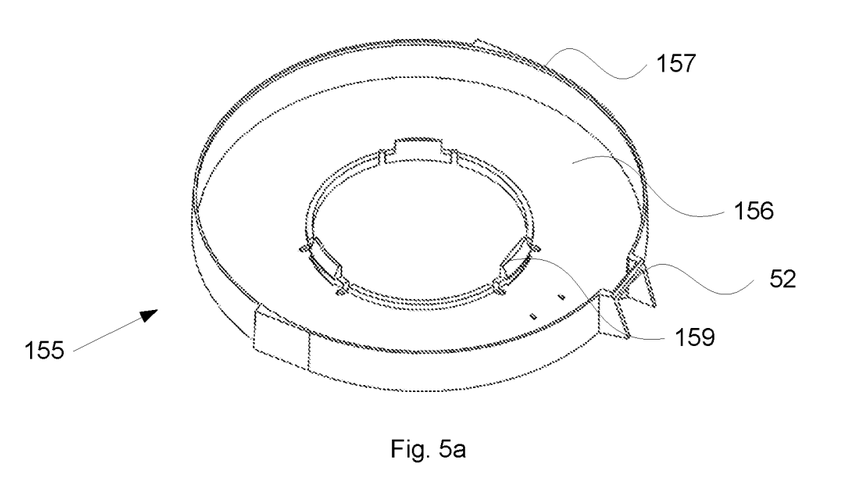
FIGS. 5a to 5c respectively show isometric views of alternative sockets for the tablet cartridge unit of FIGS. 3a to 4b.

FIG. 5a shows an isometric view of an alternative socket 155, wherein a stabilization element 52 is provided at the rim of the outer wall 157 across the opening 158 of the socket 155. The stabilization element 52 reduces the risk of undesired bending of the socket 155 in use. If such undesired bending is large enough, tablets of the tablet cartridge unit could be dispositioned or unintentionally released from the tablet cartridge unit.

Figure 5B:
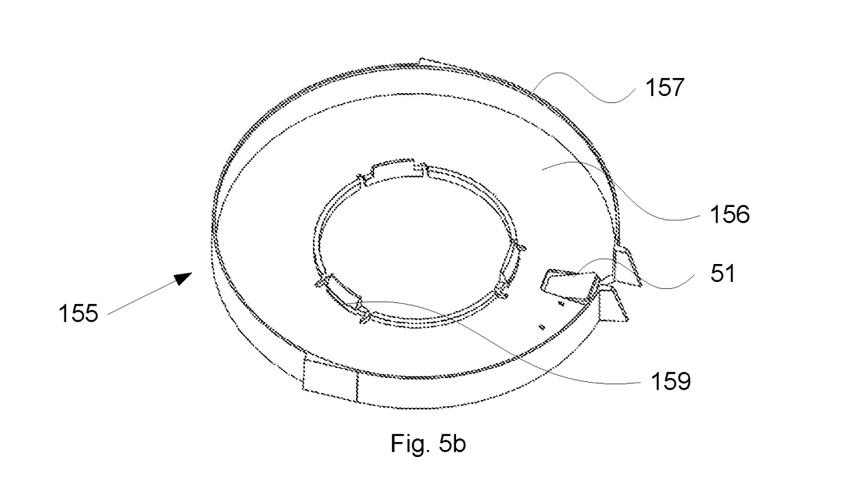

FIG. 5b shows an isometric view of an alternative socket 155, wherein said socket 155 adjacent to said opening 158, e.g. radially front of the opening, comprises a tilting plate 51. The tilting plate 51 may be spring loaded and have an idle or tilted state in which it projects or tilts into the associated tablet compartment thereby blocking the rotary movement of the adjacent flanges 154 of the compartment member 151 by the engagement of the tilting plate 51. This is particularly beneficial during transport of the assembled tablet cartridge unit 15 in use, since unintentional rotary movement between the compartment member 151 and the socket 155 may be prevented, thereby removing the risk of unintentional release of tablets from said tablet cartridge unit. The tilting plate 51 also have an aligned state, in which a top surface of the tilting plate 51 is aligned with the socket base plate 156. Hence, in the aligned state the top surface is flat with the socket base plate, there by not preventing tablets to slide towards the opening 158. The tilting plate 51 may change from its idle state to its aligned state upon mounting into the support structure 13, whereby a member (not shown) of the support member 13 engages with the bottom surface of the tilting plate 51 thereby forcing the tilting plate from its idle state to its aligned state.

Figure 5C:
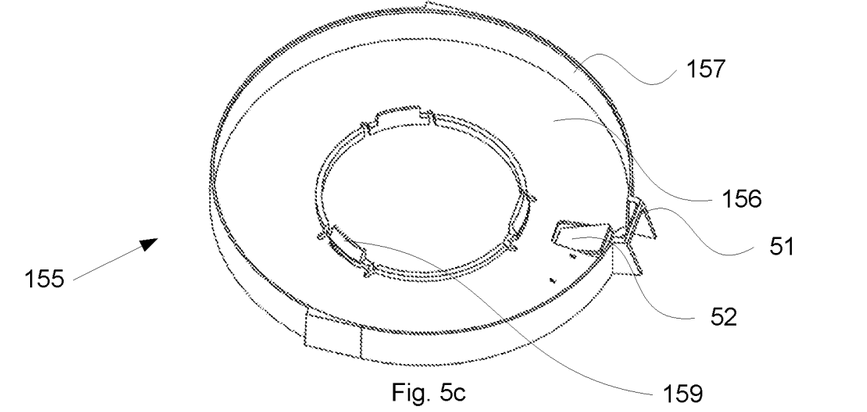

It should be appreciated that the tilting plate is not required to be provided straight in front of the opening 158 as shown in FIGS. 5b and 5c. The tilting plate 51 could be provided in the socket base plate at other positions, such as in adjacent tablet compartments sections. However, it should be appreciated that during transport it is preferred that the tablet compartment in which the tilting plate is provided is free from tablets, to prevent such tablets to fall out.

FIG. 5c shows an isometric view of an alternative socket 155 comprising both a stabilization element 52 and a tilting plate 51.

With reference to FIGS. 1a and 6a to 6c, the body 11 in a side wall thereof may be provided with an opening 16 for accessing a bottom portion of the tablet drop channel 12. A cup 30 may be introduced into the opening in use.

Figure 6A:
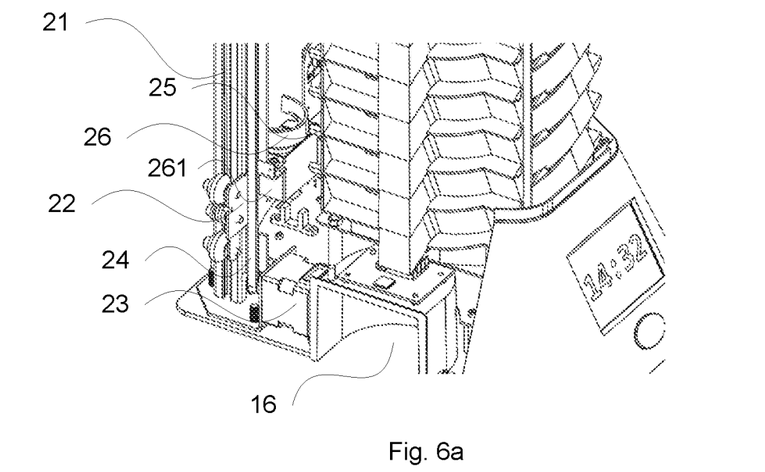
FIGS. 6a to 6c respectively show isometric views of a bottom portion of the tablet dispenser unit at different stages as a cup is introduced into the tablet dispenser unit.
Figure 6B:
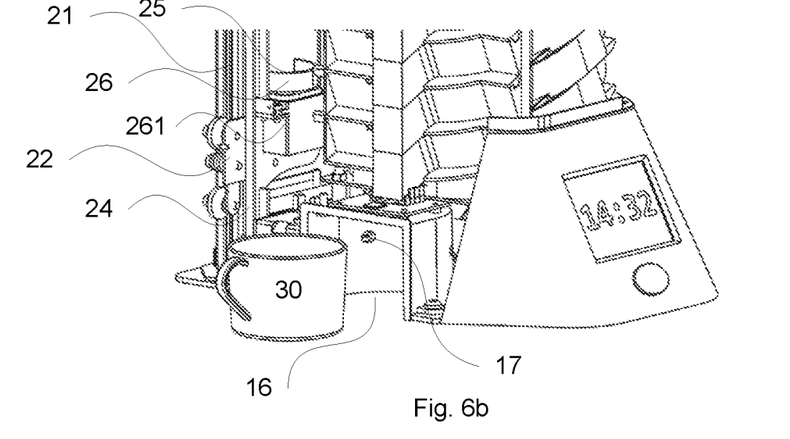
Figure 6C:
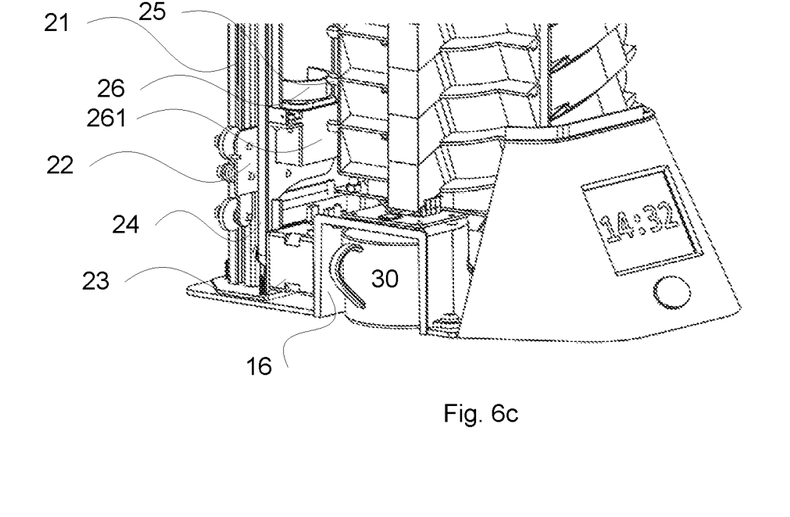

The tablet dispenser 10 may further comprise a sensor 17 for detecting the presence of a cup 30 when inserted through the opening 16. The opening 16 is in communication with the tablet drop channel.

A lift assembly 20 is arranged in the tablet dispenser 10 and arranged to move between different levels to thereby align with each tablet cartridge unit 15.

Figure 2C:
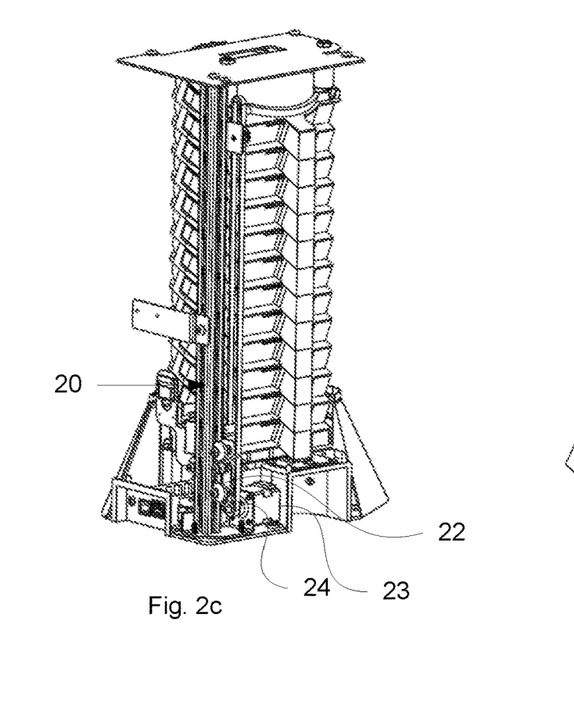
Figure 2D:
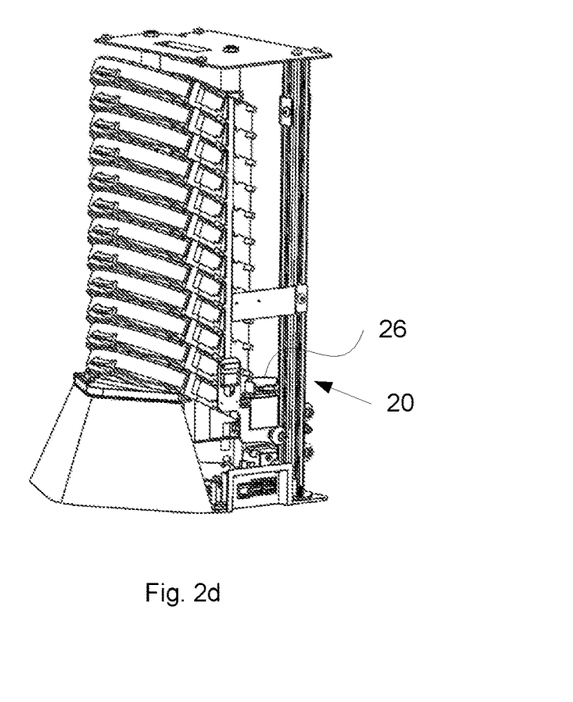

The lift assembly 20 may comprise a stationary guide rail 21. Moreover a bracket 22 is movable along the guide rail 21, by the operation of an electric motor 23 operatively coupled to the bracket 22 via an associated driving belt 24. The electric motor 23 may be an electric step motor stationary arranged in the tablet dispenser as shown in FIG. 2c. By the operation of the electric motor the driving belt 24 connected to the bracket 22 will move the bracket 22 along the guide rail 22 such as to be aligned with the associated tablet cartridge units 15 and/or cartridge receiving members 131 provided one above the other at different levels adjacent to and along the guide rail 21.

The movable member may be provided with a detector, e.g. a camera, (not shown) for detecting identity information (of the means of identification e.g. QR code, ID tag or ID label as explained above) of each tablet unit. The identity information at least comprises the type of tablets contained in the tablet cartridge unit 15, but could also include the number of tablets stored in each tablet compartment, if more than a single tablet is stored therein.

In use, the detector scans the QR code or ID label and checks it against the dosing schedule and patient information that available to a control unit of the tablet dispenser unit. The control unit, will prevent a tablet cartridge unit to be reused after running out of tablets, since the serial number of each tablet cartridge unit (optionally in conjunction with the stored use history of said tablet cartridge unit) may be stored by the control unit and be prevented from being re-used at a later stage after removal of the tablet cartridge unit from the tablet dispenser. A tablet cartridge unit with the wrong information may be prevented from being used since at least some information (e.g. patient ID, type of tablets, dosing regimen) of the tablet cartridge unit needs to match that already stored or expected by the control unit of the tablet dispenser unit. The detector may be controlled such as to scans all QR codes or ID labels each time the cover 11 of the tablet dispenser unit is closed. For this purpose a sensor for detecting when the cover 11 is closed may trigger a signal to the control unit to conduct a scan of the tablet cartridge units. It may also be arranged to scan the tablet cartridge units 15 immediately prior to dispensation of the medication.

The lift assembly 20 may be operatively associated with at least one spring loaded telescoping pushing member 25 for engaging the engagement surface 411 of the ridge pattern 41 of each tablet cartridge unit 15. In its idle state the spring loaded telescoping pushing member 25 is not in contact with the ridge pattern 41 or any of the associated engagement surfaces 411, see FIGS. 4a and 4b. The spring of the telescoping pushing member acts to move the telescoping pushing member to its idle state.

Upon engagement with a rotary member 26 of the lift assembly 20 the spring loaded telescoping pushing member may be pushed from its idle state to engage with an engagement surface 411, against the spring force of the spring, thereby rotating the compartment member 151 in relation to its socket 155 to align the next tablet compartment with the opening 158.

The rotary member 26 is thus able to both engage and disengage with the telescoping pushing member 25 in use. The rotary member 26 may have an arc shape for improving the engagement and disengagement of the telescoping pushing member. The rotary member 26 may be of an excenter type, thereby translating rotational movement of the rotary member 26 to a translational movement engaging/disengaging the telescoping pushing member 25 in use.

The rotary member 26 may be attached to the bracket 22 and its associated rotation be controlled by a servo motor 261. The axis of rotation of the rotary member may be parallel to the longitudinal extension of the guide rail 21. When the rotary member 26 returns to its idle position by the operation of the servo motor 261 it disengages from the associated telescoping pushing member 25, whereby the telescoping pushing member 25 returns to its idle state by means of the spring force of its associated spring. The servo motor 261 may also be attached to the bracket 22 thus following the movement of the bracket along the guide rail 21 upon the operation of the electric motor 23.

Hence, as the bracket 22 moves along the guide rail 21 the rotary member 26 will follow this movement. By providing a telescoping pushing member 25 in connection with each tablet cartridge unit 15, as shown in FIGS. 4a-4b, and 6a-6b, the rotary member 26 may be moved by the electric motor along the guide rail 21 to a level associated with each tablet cartridge unit 15, to allow for engagement/disengagement between the rotary member 26 and the associated telescoping pushing member 25 for each tablet cartridge unit 15 by operation of the servo motor 261.

As shown in FIGS. 4a to 4b, the telescoping pushing member 25 may be connected to the cartridge receiving members 131 of the supporting structure 13 as shown in FIGS. 4a to 4b. Moreover, the supporting structure 13 may comprise more than one cartridge receiving members 131, each arranged above the other in relation to the base 11a of the tablet dispenser. Each cartridge receiving member may comprise a hollow channel section 132 constituting a part of the tablet drop channel 12. In this way, several cartridge receiving members 131 may be stacked one above the other and together form the tablet drop channel 12 via their respective hollow channel sections 132.

It should be appreciated that the operation of the lift assembly, including the operation of the electric motor 23, the detector, the rotary member 26 and the associated servo motor 261 may be controlled using a control unit having computer processing capabilities and associated memory for storage. It should be appreciated that all software related functions of the tablet dispenser unit, e.g. operation of the display operation, saving/updating/executing dosing regimes, buttons, communication interfaces (Ethernet, USB) may be controlled by a control unit having computer processing capabilities.

What is claimed is:

1. A tablet dispenser comprising:
 a body having a base for resting on an underlying foundation in use, the body including
  a tablet drop channel extending in a direction at an angle ($\beta$) relative to a base plane formed by the base, and
  a support structure accommodating at least two tablet cartridge units arranged one above the other in relation to the base, each tablet cartridge unit having an opening allowing a tablet from the associated tablet cartridge unit to be released into the tablet drop channel via gravitational force, whereby each tablet cartridge unit is inclined at an angle ($\alpha$) relative the base plane; and
 a lift assembly that includes a bracket being arranged to move along a guide rail between different levels to thereby align with each tablet cartridge unit;
 wherein the lift assembly is operatively coupled to at least one spring loaded telescoping pushing member for engaging an engagement surface of a ridge pattern of a compartment member of each tablet cartridge unit; and wherein the lift assembly further comprises a rotary member for engaging/disengaging with the telescoping pushing member in use.

2. The tablet dispenser according to claim 1, wherein each tablet cartridge unit comprises a compartment member;

wherein the compartment member has a cylindrical cover sheet on which an inner wall is arranged; and wherein a number of flanges are arranged on the cylindrical cover sheet between the inner wall and an outer boundary of the cover sheet.

3. The tablet dispenser according to claim 2, wherein each tablet cartridge unit further comprises:

an associated socket for detachably receiving the compartment member before use;

wherein the socket includes a cylindrical socket base plate and an outer wall extending at least partly along an outer boundary of the socket base plate;

wherein the outer wall has an inner diameter being larger than the outer diameter of the cover sheet, thereby allowing the socket to embrace the compartment member in use, whereby two adjacent flanges, the inner wall, the cover sheet, the outer wall, and the socket base plate together form a tablet compartment for holding at least one tablet.

4. The tablet dispenser according to claim 3, wherein the inner wall has a cylindrical shape; and wherein the socket base plate includes means for detachably attaching the cylindrical inner wall of the associated compartment member to the socket such that the compartment member when attached is allowed to rotate in relation to the socket such as to allow for rotary alignment of each tablet compartment and the opening in use.

5. The tablet dispenser according to claim 3, wherein the cover sheet comprises a cylindrical ridge pattern provided at a side opposite that of the inner wall and flanges;

wherein the cylindrical ridge pattern has one engagement surface for each tablet compartment;

wherein the engagement surface in use is arranged to receive a force such to rotate the compartment member in relation to the associated socket, thereby aligning the opening with the next tablet compartment of the tablet cartridge unit.

6. The tablet dispenser according to claim 5, wherein the socket base plate is provided with a protrusion protruding in a direction having a component in the same direction as the outer wall; and wherein the protrusion in use is arranged to engage with one of the flanges such as to bend the flange such as to increase the size of the tablet compartment, to avoid a tablet from getting stuck in the tablet compartment when the tablet compartment is aligned with the opening.

7. The tablet dispenser according to claim 1, wherein the body in a side wall thereof further comprises an opening for accessing a bottom portion of the tablet drop channel.

8. The tablet dispenser according to claim 7, wherein the body further comprises a sensor for detecting the presence of a receiving cup when inserted through the opening for accessing a bottom portion of the tablet drop channel.

9. The tablet dispenser according to claim 1, wherein the lift assembly comprises a detector for detecting identity information of each tablet unit; and wherein the identity information at least includes the type of tablets contained in the tablet cartridge unit.

10. The tablet dispenser according to claim 1, wherein the supporting structure comprises at least two cartridge receiving members, each arranged above the other in relation to the base;

wherein each cartridge member includes a hollow channel section constituting a part of the tablet drop channel.

11. The tablet dispenser according to claim 3, wherein the socket base plate adjacent to the opening comprises a tilting plate having an idle state in which it projects into the associated tablet compartment thereby blocking the rotary movement of the adjacent flanges of the compartment member by the engagement of the tilting plate during transport of the assembled tablet cartridge unit in use.

12. The tablet dispenser according to claim 3, wherein a stabilization element is provided at the rim of the outer wall across the opening of the socket.

* * * * *